United States Patent
Banting et al.

(10) Patent No.: US 6,410,007 B1
(45) Date of Patent: *Jun. 25, 2002

(54) ANTAGONISM OF ENDOTHELIN ACTIONS

(75) Inventors: James D. Banting, Kingston; Jeremy P. W. Heaton, Gananaque; Michael A. Adams, Kingston, all of (CA)

(73) Assignee: Queen's University at Kingston (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/152,874

(22) Filed: Sep. 14, 1998

Related U.S. Application Data

(63) Continuation of application No. PCT/CA97/00169, filed on Mar. 13, 1997, which is a continuation-in-part of application No. 08/615,659, filed on Mar. 13, 1996, now Pat. No. 5,688,499.

(51) Int. Cl.[7] .......................... A61K 49/00; A61K 38/00; A61N 31/17; G01N 31/00
(52) U.S. Cl. .......................... 424/78.35; 424/92; 514/2; 514/12
(58) Field of Search .......................... 514/4, 2, 44, 12; 536/24.5, 44; 424/9.2, 78.35

(56) References Cited

U.S. PATENT DOCUMENTS

| | | |
|---|---|---|
| 5,284,828 A | 2/1994 | Hemmi et al. |
| 5,338,726 A | 8/1994 | Shiosaki et al. |
| 5,378,715 A | 1/1995 | Stein et al. |
| 5,382,569 A | 1/1995 | Cody et al. |
| 5,688,499 A | 11/1997 | Banting et al. |

FOREIGN PATENT DOCUMENTS

| | | |
|---|---|---|
| WO | WO93/21219 | 10/1993 |
| WO | WO96/00738 | 1/1996 |

OTHER PUBLICATIONS

Banting et al. "Increased endothelin activity plays a primary role in hypertension induced by acute nitric oxide synthase blockade", FASEB Journal, v.9 (3) pA338, Mar. 1995.*
Wang et al. Involvement of endothelin–1 in hypoxic pulmonary vasoconstriction in the lamb Journal of Physiology, v.482 (2) pp. 421–434, Jan. 1995.*
Teerlink et al. Role of endothelin in the maintainance of blood pressure in concious rats with chronic heart failure, Circulation v.90 (5), pp. 2510–2518, Nov. 1994.*
Agrawal, TIBTech, vol. 14, pp. 376–387, Oct. 1996.*
Branch, TIBS 23, p. 45–50, Feb. 1998.*
Luscher, Drugs of Today, vol. 31, Suppl. B, p 7–17, 1995.*
Garg, U.C. and Hassid A., "Nitric Oxide Decreases Cytosolic Free Calcium in Balb/c 3T3 Fibroblasts by a Cyclic GMP–independent Mechanism," *J. Biol. Chem.*, 226(1):9–12(1991).

(List continued on next page.)

*Primary Examiner*—Andrew Wang
*Assistant Examiner*—Karen A. Lacourciere

(57) ABSTRACT

The mechanism of hypertension following acute NO synthase blockage is via endothelin-mediated vasoconstriction. Thus, NO appears to inhibit endothelin activity by blocking its expression and not as a chronic direct acting vasodilator. Administration of an endothelin antagonist to a patient in a 'normal' physiological state may result in specific regional vasodilation. This treatment finds utility in the treatment of erectile dysfunction.

11 Claims, 4 Drawing Sheets

OTHER PUBLICATIONS

Garg, U.C. and Hassid A., "Nitric Oxide–generating Vasodilators and 8–Bromo–Cyclic Guanosine Monophosphate Inhibit Mitogenesis and Proliferation of Cultured Rat Vascular Smooth Muscle Cells," *J. Clin. Invest.*, 83:1774–1777 (1989).

Palmer, R.M.J., et al., "Nitric oxide release accounts for the biological activity of endothelium–derived relaxing factor," *Nature*, 327:524–526 (1987).

Assender, J.W., et al., "Does Nitric Oxide Inhibit Smooth Muscle Proliferation?," *J. Cardiovasc. Pharmacol.*, 17(Suppl.3): S104–S107 (1991).

O'Connor, K.J., et al., "Nitrovasodilators Have Proliferative as Well as Antiproliferative Effects," *J. Cardovasc. Pharmacol.*, 17(Supp.3):S100–S103 (1991).

Farhy, R.D., et al., "Role of Kinins and Nitric Oxide in the Effects of Angiotensin Converting Enzyme Inhibitors on Neointima Formation," *Cir. Res.*, 72(6):1202–1210 (1993).

Arnal, J–F, et al., "Determinants of Aortic Cyclic Guanosine Monophosphate in Hypertension Induced by Chronic Inhibition of Nitric Oxide Synthase," *J. Clin. Invest.*, 90:647–652 (1992).

Manning, R. D., Jr. et al., "Role of Nitric Oxide in Long–term Angiotensin II–Induced Renal Vasoconstriction," *Hypertension*, 21(6) Part 2:949–955 (1993).

Manning, R. D., Jr. et al., "Cardiovascular Responses to Long–term Blockade of Nitric Oxide Synthesis," *Hypertension*, 22(1):40–48 (1992).

Morton, J.J., et al., "Persistent hypertension following inhibition of nitric oxide formation in the young Wistar rat: role of renin and vascular hypertrophy," *J. Hypertension*, 11:1083–1088 (1993).

Richard V., et al., "In Vivo Evidence of an Endothelin–Induced Vasopressor Tone After Inhibition of Nitric Oxide Synthesis in Rats," *Circ.*, 91(3):771–775 (1995).

Schiffrin, E.L., et al., "Deoxycorticosterone Acetate Plus Salt Induces Overexpression of Vascular Endothelin–1 and Severe Vascular Hypertrophy in Spontaneously Hypertensive Rats," *J. Hypertension*, 25(4),Part 2:769–773 (1995).

Schiffrin, E.L., and Thibault, G., "Plasma Endothelin in Human Essential Hypertension," *Am. J. Hypertension*, 4(4), Part 1:303–308 (1991).

Weber, H., et al., "Endothelin–1 and Angiotension–II Stimulate Delayed Mitogenesis in Cultured Rat Aortic Smooth Muscle Cells: Evidence for Common Signalin Mechanisms," *Mol. Endo.*, 8(2):148–157 (1994).

Eddahibi, S., et al., "Protection from pulmonary hypertension with an orally active endothelin receptor antagonist in hypoxic rats," *Am. J. Physiol.*, 268(2):H828–H835 (1995).

Feldman, H. A., et al., "Impotence and Its Medical and Psychosocial Correlates: Results of the Massachusetts Male Aging Study," *J. Urol.*, 151:54–61 (1994).

Shabsigh, R., et al., "Evaluation of Erectile Impotence," *Urology*, XXXII(2):83–90 (1988).

Whitehead, E.D., "Diabetes–related impotence: Putting new knowledge to waste," *Geriatrics*, 43(2):114 (1988).

Furlow, W. L., et al., "Q & A, Prevalence of impotence in the United States," *Med. Aspects Human Sexuality*, 19(1):13–16 (1985).

Raifer, J., et al., "Nitric Oxide as a Mediator of Relaxation of the Corpus Cavernosum in Response to Nonadrenergic, Noncholinergic Neurotransmission," *New Engl. J. Med.*, 326(2):90–94 (1992).

Saenz de Tejada, I., et al., "Cholinergic neurotransmission in human corpus cavernosum. I. Responses of isolated tissue," *Am. J. Physiol*, 254:H459–H466 (1988).

de Groat, W.C., and Steers, W.D., "Neuroanatomy and Neurophysiology of Penile Erection" In: Contemporary Management of Impotence and Infertility (Tanagho, E.A., Lue, T.F., McClure, R.D., Eds.), Williams and Wilkins (1988).

Lue, T.F. and Tanagho, E.A., "Physiology of Erection and Pharmacological Management of Impotence," *J. Urol.*, 137(5):829–835 (1987).

Juenemann, K–P., et al., "Hemodynamics of Papaverine– and Phentolamine–Induced Penile Erection," *J. Urol.* 136(1):158–160 (1986).

Lue, T.F., et al., "Hemodynamics of Erection in the Monkey," *J. Urol.*, 130:1237–1241 (1983).

Weiss, H.D., "The Physiology of Human Penile Erection," *Ann. Intern. Med.*, 76:793–799 (1972).

Juenemann, K.–P., et al., Neurophysiological Aspect of Penile Erection: the Role of the Sympathetic Nervous System, *British J. Urol.* 64:84–92 (1989).

Melman, A. and Henry, D., The Possible Role of the Catecholamines of the Corpora in Penile Erection, *J. Urol.*, 121:419–421 (1979).

Benson, G.S., et al., "Neuromorphology and Neuropharmacology of the Human Penis," *J. Clin. Invest.*, 65:506–513 (1980).

Hedlund, H. and Andersson, K–E. "Contraction and Relaxation Induced by Some Prostanoids in Isolated Human Penile Erectile Tissue and Cavernous Artery," *J. Urol.*, 134:1245–1250 (1985).

Wagner, G., and Brindley, G.S., Chapter 10: "The effect of atrophine $\alpha$ and $\beta$ blockers on human penile erection: A Controlled Pilot Study" In: *Vasculogenic Impotence* (Zorginotti, A. W., Rossi, G., Eds.) Charles C. Thomas: Springfield, Ill., 77–81 (1980).

Adaikan, P.G., et al., "Cholinoreceptors in the Corpus Cavernosum Muscle of the Human Penis," *J. Auton, Pharm.*, 3:107–111 (1985).

Ignarro, L.J., et al., "Nitric Oxide and Cyclic GMP Formation Upon Electrical Field Stimulation Cause Relaxation of Corpus Cavernosum Smooth Muscle," *Biochem. Giophys. Res. Commun.*, 170(2):843–850 (1990).

Gu, J., et al., "Peptidergic Innervation of the Human Male Genital Tract," *J. Urol.*, 130:386–391 (1983).

Gu, J., et al., "Decrease of Vasoactive Intestinal Polypepetide (VIP) in the Penises from Impotent Men," *Lancet*, 2:315–318 (1984).

Willis, E.A., et al., "Vasoactive Intestinal Polypeptide (VIP) as a Putative Neurotransmitter in Penile Erection," *Life Sci.*, 33:383–391 (1983).

Steif, C.G., et al., "A Possible Role for Calcitonin–Gene–Related Peptide in the Regulation of the Smooth Muscle Tone of the Bladder and Penis," *J. Urol.*, 143(2):392–397 (1990).

Li, J–S., and Schiffrin, E.L., "Chronic endothelin receptor antagonist treatment of young spontaneously hypertensive rats," *J. Hypertension*, 13(6):647–652 (1995).

Heaton, J.P.W., et al., "The Characterization of a Bio–Assay of Erectile Function in a Rat Model," *J. Urol.*, 145:1099–1102 (1991).

Parkkisenniemi U.–M. and Klinge, E., Functional Characterization of Endothelin Receptors in the Bovine Retractor Penis Muscle and Penile Artery, *Pharmacology & Toxicology*, 79(2):73–79 (1996).

Christ, G.J. et al., "Pharmacological studies of human erectile tissue: characteristics of spontaneous contractions and alterations in a–adrenoceptor responsiveness with age and disease in isolated tissues," *J. Pharmacol. 101*:375–181 (1990).

Christ, G.J. et al., "Endothelin–1 as a Putative Modulator of Erectile Dysfunction: I. Characteristics of Contrction of Isolated Corporal Tissue Strips," *J. Urology 153*:1998–2003 (1995).

Saenz de Tejada, I. et al., "Endothelin: localization, synthesis, activity, and receptor types in human penile corpus cavernosum," *Am. J. Physiol.*, 261:H1078–H1085 (1991).

Holmquist, F. et al., "Functional Effects, Binding Sites and Immunolocalization of Endothelin–1 in Isolated Penile Tissues from Man and Rabbit," *J. of Pharmacol. Exp. Ther.*, 261(2):795–802 (1992).

Holmquist, F. et al., "Actions of endothelin on isolated corpus cavernosum from rabbit and man," *Acta Physiol. Scand 139*:113–122 (1990).

Lerner, S.E. et al., "Endothelin as a Putative Modulator of Erectile Dysfunction," Abstract 286, *J. Urol.*, 149:285A(1993).

Andersson, K–E and Wagner, G., "Physiology of Penile Erection," *Physiol. Rev.*, 75:191–236 (1995).

Ari, G. et al. "Possible role for endothelins in penile erection," *Eur.J.Pharmcol.*, 307:69–74 (1996).

Bell,C.R.W. et al., "The density and distribution of endothelin 1 and endothelin receptor subtypes in normal and diabetic rat corpus cavernosum," *Brit. J. Urol. 76*:203–207 (1995).

Banting, J.D. et al., "Acute hypertension after nitric oxide synthase inhibition is mediated primarily by increased endothelin vasoconstriction," *J. Hyperten. 14*:975–981 (1996).

Francavilla, S. et al., "Endothelin–1 in Diabetic and Non-diabetic Men with Erectile Dysfunction," *J. Urol. 158*:1770–1774 (1997).

Holmquist, F. et al., "Phospholipase C Activation by Endothelin–1 and Noradrenaline in Isolated Penile Erectile Tissue From Rabbit," *J. Urol. 147*:1632–1635 (1992).

Kim, D C, et al., "Endothelin–1–induced modulation of contractile responses elicited by an $\alpha_1$–adrenergic agonist on human corpus cavernosum smooth muscle," *Int. J. Impot. Res. 8*:17–24 (1996).

Kim, N N, et al., "Altered contractility of rabbit penile corpus cavernosum smooth muscle by hypoxia," *J. Urol.*, 155(2):772–778 (1996). Abstract.

Kourembanas, S. et al., "Nitric Oxide Regulates the Expression of Vasoconstrictors and Growth Factors by Vascular Endothelium under both Normoxia and Hypoxia," *J. Clin. Invest. 92*:99–104 (1993).

Moncada, S. et al., "Nitric Oxide: Physiology, Pathophysiology, and Pharmacology," *Pharmacol. Rev. 43(2)*:109–134 (1991).

Parkkisenniemi, U.–M. and Klinge, E., "Functional Characterization of Endothelin Receptors in the Bovine Retractor Penis Muscle and Penile Artery," *Pharmacol. Toxicol. 79*:73–79 (1996).

Pollock, D.M. et al., "Angiotensin Blockade Reverses Hypertension During Long–term Nitric Oxide Synthase Inhibition," *J. Hyperten. 31*:660–666 (1993).

Pucci, M.L. et al., "Pressor and Renal Vasoconstrictor Effects of $N^G$–Nitro–L–Arginine as Affected by Blockade of Pressor Mechanisms Mediated by the Sympathetic Nervous System, Angiotensin, Prostanoids and Vasopressin," *J. Pharmacol. Exp. Ther. 261(1)*:240–245 (1992).

Stewart, D. J., "Impact of Endothelin–1 on Vascular Structure and function," A Symposium: Vascular Biology Working Group pp. 145–146 (1998).

Sullivan, M.E. et al., "Alterations in Endothelin B Receptor Sites in Cavernosal Tissue of Diabetic Rabbits: Potential Relevance to the Pathogenesis of Erectile Dysfunction," *J. Urol. 158*:1966–1972 (1997).

Zhao, W. and Christ, G.J., "Endothelin–1 as a Putative Modulator of Erectile Dysfunction. II. Calcium Mobilization in cultured Human Corporal Smooth Muscle Cells," *J. Urol. 154*:1571–1579 (1995).

\* cited by examiner

ANTAGONISM OF ENDOTHELIN ACTIONS

RELATED APPLICATIONS

This application is a Continuation of PCT/CA97/00169, filed Mar. 13, 1997, which is a Continuation-in-Part application of U.S. Ser. No. 08/615,659, filed Mar. 13, 1996, now U.S. Pat. No. 5,688,499. The contents of these applications are incorporated herein by reference in their entirety.

FIELD OF THE INVENTION

This invention relates to methods for down-regulating local endothelin-mediated vasoconstrictor and/or vascular growth activity in "apparently" normal physiological conditions in order to re-establish normal control in specific regions of the circulation which demonstrate pathophysiology. More particularly this invention relates to the administration of agents which antagonize the expression or activity of endothelin for the treatment of abnormalities of specific regions of the vasculature such as in erectile dysfunction in male patients.

BACKGROUND OF INVENTION

Endothelins were first described in 1988 and have been shown to be powerful vasoconstrictors, predominantly found in the vascular endothelium and, since that time, numerous endothelin antagonists and pharmaceutically acceptable salts thereof have been identified and can be obtained commercially (e.g., Sigma, American Peptides). Attention is also directed to U.S. Pat. No. 5,284,828 issued Feb. 8, 1994 to Hemmi et al., U.S. Pat. No. 5,378,715 issued Jan. 3, 1995 to Stein et al. and U.S. Pat. No. 5,382,569 issued Jan. 17, 1995 to Cody et al., which describe in detail the chemical structures of various endothelin antagonists, and to U.S. Pat. No. 5,338,726 issued Aug. 16, 1994 to Shinosaki et al., which describes the chemical structure of endothelin converting enzyme inhibitors, the disclosures of which are incorporated herein by reference. To date, however, antagonists of endothelin have not been approved for therapeutic use, although a number of investigators have postulated that endothelin antagonists could be used for conditions ranging from renal failure, endotoxic shock, asthma, angina, or diabetes to pulmonary hypertension and possibly other indications.

Under normal physiological conditions, endothelin can be found in almost all parts of the circulation at very low levels. In general, in the normal rodent circulation endothelin (ET) is not found in elevated quantities and appears to have minimal effect in the normal regulation of vascular tone, i.e., there is no appreciable decrease in blood pressure when an endothelin antagonist is administered by injection in normal circulation. Further, at present there does not appear to be any evidence suggesting that ET plays a physiological role even in a small portion of the circulation under normal conditions in experimental models. However, it is likely that the circulation may appear normal when in fact a specific region of the circulation reveals pathophysiological changes, such as occurs with erectile dysfunction. Penile erection demands specific local vasodilation and/or inhibition of local vasoconstrictor mechanisms. It is not surprising that findings of elevated levels of endothelin in the blood are not widespread, as the regulation of ET action indicates a release preferentially towards the smooth muscle side, away from the circulation. In addition, it is highly improbable that there would be increased ET found in the circulation resulting from increased activity in a small portion of the circulation. ET is known to have a very short half-life.

It is widely known that administration of nitric oxide (NO) can provoke powerful vasodilator responses. The chronic role of nitric oxide synthase (NOS) as a vasodilator has only been inferred by indirect means, i.e., by removal of the NOS activity. Endogenously, there is much more redundancy in control of vasodilatation. For example, vasodilation can be induced by acetylcholine, bradykinin, adenosine triphosphate (ATP), histamine, vasoactive intestinal polypeptide (VIP), and leukotrienes, amongst others. The actions of these endogenous modulators have been shown to be dependent on the presence of the endothelium, an effect likely mediated by endothelial derived relaxing factor/NO (EDRI/NO) (1,2,3). Other vasodilator mechanisms exist which are not endothelium dependent, such as $\beta_2$-adrenergic, arial natriuretic peptide (ANP) and certain prostaglandins. The actions of NO appear to be mostly cGMP-mediated via guanylate cydase activation, although other mechanisms have been suggested. Garg and Hassid (1, 2) and others (4,5) demonstrated a difference in the effects of NO-generating vasodilator agents in inhibiting vascular smooth muscle cell growth in culture; however, it is clear that NO can act not only as a vasodilator but also to inhibit vascular growth responses in a number of conditions (6).

In the last several years a large number of studies has demonstrated that decreased NO production using inhibitors of NO synthase (e.g., $N^\omega$-nitro-L-arginine-methyl ester or L-NAME) produces dose-dependent hypertension (i.e., L-arginine reversible, and which correlates with decreased cyclic guanosine monophosphate (cGMP)) (7,8,9). Data from Schiffrin's (4,10) and Morton's (11) groups demonstrate that prolonged high dose L-NAME hypertension is associated with hypertrophic changes in the mesenteric vasculature (1 media thickness and 1 media/lumen ratio). Interestingly, Schiffrin's group found that the degree of change in vascular structure was less marked than in other models (2K1C) with equivalent hypertension and of a similar duration. Taken together with the findings of NO development of cardiac hypertrophy and slower vascular changes, current evidence indicates that L-NAME hypertension is quite different from other models. Further, although these findings could suggest a role for NO as a modulator of vascular structure, our recent findings suggest that NO may play a more important inhibitory role in suppressing the activity of the endothelin vasoconstrictor system. The concept of NO suppression of ET expression is further supported by evidence both from Luscher's group in vitro and from the Clozel group (12) in vivo showing that there is increased release of ET from endothelial cells after NOS blockage. These data suggest that exogenous administration of NO synthase antagonists produces a condition wherein the lack of NO appears to be a modulator of ET expression and release. Recent findings, in particular from Schiffrin's group (13,14), in deoxycorticosterone acetate (DOCA)-salt hypertension point to a trophic role for endogenous endothelin in the development of vascular structural changes. They found that there is increased ET-1 gene expression and immunoreactivity in blood vessels, but not in the plasma, of DOCA-salt hypertensive rats, whereas renin angiotensin system (RAS) activity was decreased. There was a substantial development of vascular hypertrophy in the DOCA-salt model which was markedly attenuated by treatment with an $ET_A/ET_B$ receptor antagonist. The concept that ET-1 is a vascular trophic factor is further supported by findings in studies with cultured vascular smooth muscle cells showing that addition of endothelin produces a mitogenic response (15), as well as findings in other in vivo studies indicating a role in structural changes associated with pulmonary hypertension (16). ET-1 is approximately 100 times more potent as a vasoconstrictor than Ang II or catecholamines. Interestingly, in the culture studies, although the maximal growth response to ET-1 was less than half of that for Ang II, the combination of ET-1 plus Ang II provoked a greater mitogenic response than either peptide alone. We are not aware of any studies that have assessed the in vivo cardiovascular growth responses to direct endothelin infusion.

An important aspect of the invention derives from the development of a concept which reveals an interrelationship between NO activity and endothelin vasoconstrictor activity, in vivo: specifically, that NO acts primarily as a chronic inhibitor of endothelin-mediated vasoconstriction, and less as a chronic vasodilator. Accordingly, it is proposed that endothelin plays a role in disease conditions associated with impaired NO synthesis, particularly if the pathophysiology is restricted to a specific portion of the circulation; i.e., if the entire circulation were altered, numerous compensatory changes in neurohumoral systems would also occur.

Our hypothesis is that if NO synthesis is inhibited, a significant increase in mean arterial pressure (MAP) is the result of increased endothelin release and this MAP increase can be eliminated by administration of an endothelin antagonist. It is apparent, therefore, that administration of an endothelin antagonist in physiological conditions where NO production is inhibited will result in vasodilation ONLY in the regions which have upregulated ET activity consequent, in part, to a down regulation of local NO production. Physiological conditions where NO production is inhibited in a local circulation, such as male erectile dysfunction, indicate that suppression of endothelin activity would offer an effective treatment.

Based on the understanding that a significant portion of the underlying problem in clinical erectile function relates to "vascular" mechanisms, much of the current state-of-the-art research involves determining the contribution that the different vascular effector control systems make in normal and pathophysiological states. There is substantial understanding of the hemodynamic events that lead to an erection, and yet the quantitative roles of each of the neuroeffector, humoral and local systems in these events remain poorly described. Since 1990, nitric oxide (NO) has been considered the primary non-adrenergic non-cholinergic neurotransmitter in the penis and has been presumed to be the primary mediator of corporal relaxation during erection.

The issue of "impotence" was discussed at the National Institutes of Health (NIH) in Washington in December 1992 (defined as "a pattern of persistent or recurrent inability to develop or maintain an erection of sufficient rigidity for successful coitus") and has clearly been identified as having a wide range of causative or associated factors. The Massachusetts Male Aging Study (MASS) has provided us with an updated view of the epidemiology of erectile dysfunction although there seem to be some unchangeable truths—it is accepted that the prevalence of impotence increases with age (Kinsey, 1948) (17). Complete erectile dysfunction (ED) increases from 5 to 15% between 40 and 70 years of age, Feldman, 1994 (18). ED has been shown to be "directly correlated with heart disease, hypertension, diabetes, associated medications, indices of anger and depression, and inversely with serum dehydroepiandosterone, high density lipoprotein, cholesterol and an index of dominant personality."

It is now estimated that in North America there are more than 30,000,000 men with ED, a significant increase from the figure of 10,000,000 used just 10 years ago (Shabsigh et al., 1988 (19); Whitehead, 1988 (20); Furlow, 1985 (21)). From these figures it is also reasonable to estimate that as many as three million Canadian men may have a degree of ED. The direct cost of treating impotence is impressive. Reliable figures for 1985 show that the cost of treating impotence exceeded 146 million dollars in the United States in that year alone (National Center for Health Statistics) and this number is just the estimated market size for one type of injectable therapy. The secondary effects and indirect costs associated with erectile dysfunction would suggest that impotence and sexual dysfunction are medical icebergs, The consequences of sexual dysfunction may be seen in strains on the host relationship potentially leading to marital breakdown, violence, work related sequelae, deviant sexual behavior, and impacts on children, when present, that can carry the damage into a new generation of unwanted behaviors. If ED underlies even a small but significant percentage of marital and family breakdown, then it adds vastly to the social and economic burden in society. The pragmatic issue is that large numbers of men are now being treated for ED and most of the treatments are fairly blunt instruments (intracavernosal injection (ICI) of mixed vasoactive compounds, penile prosthesis insertion) with significant cost and complications (ICI: pain, priapism, dislike of the technique; prostheses: reoperation, infection, distortion of body image).

As a medical and scientific problem, ED gained greatly in stature when Rajfer et al. (1992) (22) published their information linking nitric oxide (NO) with normal erectile function. It was an interesting coincidence that NO became "Molecule of the Year" that same year as a result of the accumulated and established work in other vascular systems. This heralded a new maturity in the study of ED—suddenly the principles of normal vascular biology (NVB) became accepted as the underpinnings of erectile physiology.

The Physiological Basis of Penile Erection

The stimulus to erection is central and neural in origin. A fully functional penile erection requires coordinated input from various levels of the central nervous system and at least three sets of peripheral nerves (thoracolumbar sympathetic, saccral parasympathetic, and pelvic somatic). Adrenergic, non-adrenergic and non-adrenergic non-cholinergic neurotransmitter systems of importance have been identified in the cavernous tissue (Saenz de Tejada, 1988) (23). An excellent account of the neural processes (without specific roles) involved in the production of a penile erection can be found in the review by deGroat and Steers (1988) (24).

A penile erection is dependent upon the integration of anatomic, vascular (hydraulic; arterial and venous), endocrine, neurologic and hormonal mechanisms. The erectile components of the penis are the corpora cavernosa and the corpus spongiosum. The latter contributes little to the rigidity of the penis when erect. The corpora cavernosa are paired cylinders that are firmly and separately anchored to the inferior pubic rami at their proximal roots, where they are covered by striated muscle (ischiocavernosus), become joined in the proximal pendulous shaft and fenestrated (i.e., functionally connected) distally. There is usually one supplying end-artery per cavernosal body, from the internal iliac artery, that branches to become the deep penile artery which has at least two types of branches within the cavernosa: The venous drainage of the corpora is through the intermediate system for the distal cavernosa and glans and through the deep system for the remaining cavernosae. The critical venous channels are the subtunical veins, which empty through emissary veins that pass through the tunica and drain into the deep dorsal vein. It is the emissary veins that are compressed during erection and permit the "locked" state of veno-occlusion.

It is well established that, for erection, neurally mediated (autonomic) vasodilation of the penile arterial blood vessel and the trabecular meshwork takes place (Lue et al., 1987) (25) permitting extra blood flow into the cavernous bodies of the penis. The expanding intracorporal volume traps the effluent veins that lie between the erectile tissue and the surrounding, relatively inelastic, fibrous tunica albuginea. The outflow capacity is thereby decreased and entrapment of blood ensues, resulting in the transformation of the flaccid penis into its erect state (Juenemann et al., 1986 (26); Lue et al., 1987 (25); Lue et al., 1983 (27); Weiss, 1980 (28)). Inflow arterial tone is of absolute importance in this process, although adequate driving blood pressure (BP) is a necessary factor. The converse, detumescence, is mediated by the sympathetic nervous system (Saenz de Tejada, 1988 (23); Juenemann et al., 1989 (29)) and is dependent on the metabolic viability of cells within the erectile tissue. A maximal direct pharmacological vasodilator stimulus may not produce an erection in a penis driven by the high sympathetic nervous system activity state induced by fear. Thus, it is not surprising that alterations in blood flow and vascular dynamics, whether produced by decreased cardiac output, reflex sympathetic hyperactivity, atherosclerosis, untreated hypertension, antihypertensive medication or, as herein proposed, increased local endothelin-mediated vasoconstriction, can produce profound effects on the ability of the flaccid penis to be transformed into the erect state.

Penile Control Systems

The known control systems for erection are conventionally described under the 3 headings: adrenergic, cholinergic and non-adrenergic non-cholinergic (NANC). Adrenergic nerve fibers and high concentrations of norepinephrine can be found in the corpora (Melman and Henry, 1979 (30); Benson et al., 1980 (31)) and the contractile properties of phenylephrine are established unequivocally (Hedlund et al., 1984 (32); Christ et al., 1990 (33)) with post-synaptic α1 effects acting directly and pre-synaptic α2 modulation. Previously, parasympathetic nerves were thought to be the nerves responsible for erection (Wagner et al., 1980 (34)), although the in vitro effects from acetylcholine (ACh) were varied in early experiments (Adaikan et al., 1983 (35); Hedlund et al., 1985 (32)). Further, simple intracorporal injection of acetylcholine does not cause erection and atropine does not block it (Wagner et al., 1980) (34). Thus, cholinergic nerves are described as modulators of neural function. Accordingly, NANC innervation, as the pre-eminent player in erectogenesis, has received intense scrutiny and the current thinking is that nitric oxide has replaced VIP as the prime vasodilator of this system in the penis. This view was first published by Ignarro et al. (36) and has been re-stated many times since. Not surprisingly, a variety of other NANC systems have also been shown to play a role in erectile function, including vasoactive intestinal polypeptide (VIP) (Gu et al., 1983 (37) &4 (38); Willis et al., 1983 (39)), calcitonin gene related peptide (CGRP) (Stief, 1990) (40) and the prostaglandins (Hedlund and Andersson,. 1985) (41). The terms that have been used to describe the neuro-effector systems and the roles they play provide an historic basis for descriptions of penile systems but have not removed the confusion that is found in the more than 100 relevant papers that have been published since 1990 on neural regulation. It is without doubt that penile erections occur when arterial dilation and smooth muscle relaxation take place. The penis is an ideal vascular bed to consider in terms of the physiological opposition of neural effector systems involved in both relaxation and contraction i.e the penis is one of only a small handful of special circulations with dual vasoconstrictor and vasodilator neural control systems. To fully characterize the penile control systems, a greater understanding of the countervailing systems both in a clinical and an experimental setting is required in order to elucidate the critical balance and interdependence that are essential for normal function.

As described, in order for penile tumescence to occur, the pudendal vascular bed must vasodilate to shunt blood flow to the cavernosal tissue. Normal vascular beds have a balance of vasodilators and vasoconstrictors regulating the level of vascular tone. Upsetting of this balance can lead to an enhanced chronic vasoconstrictor response. Chronic erectile dysfunction creates a situation where the penile vascular bed has seen chronic low oxygen partial pressures $pO_2$. Low $pO_2$ has been shown to decrease the activity of NO synthase and hence NO production. Further, it has also been shown, in rats, that the activity of the NO synthase enzyme decays with age. Both of these concepts in combination with our novel findings indicate a key role for enhanced endothelin-mediated vasoconstriction. Once enhanced endothelin occurs, there are three levels of mechanisms that will sustain the erectile dysfunction: (i) enhanced vasoconstriction in the penile vascular bed occurs, making it more 'difficult' for the vasodilators to shunt blood to the penis to facilitate cavernosal filling (this is also a positive feedback loop with respect to NO synthase since less blood flow will maintain low $pO_2$ values); (ii) endothelin has been shown in vitro and in vivo to promote cardiovascular growth processes. This could lead to a structural change where blood vessels grow and encroach on the lumen, leading to increased resistance due to a structural mechanism (as opposed to chronic vasoconstriction); and (iii) enhanced endothelin may act as a 'primer' for other vasoconstrictor systems (renin-angiotensin system and sympathetic nervous system) which additionally act as trophic factors (i.e., the endothelin may prime the vascular bed such that Ang II, for example, will promote growth at doses that by themselves would not normally induce growth processes).

In summary, an upregulation of endothelin actions occurs when the production of NO is inhibited. This chronic enhanced endothelin, we propose, will be involved in mediating the changes leading to erectile dysfunction. Acutely, there will be enhanced vasoconstriction via the endothelium (endothelin) and, in the longer term, endothelin-mediated growth responses in the vascular tissue. The penile vascular tissue would, therefore, go through a structural change such that it would become more and more difficult to cause vasodilation with the progression of encroachment into the lumen of the vessels leading to the penis, as well as in the corpus cavernosal tissue itself.

There are several approaches that lead to the down regulation of the activity of endothelin, namely (a) peptide antagonists such as PD145065 (Parke Davis), (b) non-peptide antagonists such as bosentan (Hoffman-LaRoche) (42), (c) inhibitors of endothelin converting enzyme, such as for example phosphoramidon (i e., blocking production of endothelin) and (d) antisense oligonucleotides which specifically block the translation of the endothelin protein at the genetic level, i.e., disrupt the normal cycle of events with preproendothelin mRNA.

SUMMARY OF THE INVENTION

Thus, it is an object of the present invention to provide a method for treating physiological conditions in which NO production is at least partially inhibited, such as, but not limited to, erectile dysfunction (ED).

Another object of this invention is to provide compositions of matter for the treatment of physiological conditions in which NO production is at least partially inhibited.

By one aspect of this invention, there is provided a method for treating physiological conditions in which NO production is at least partially inhibited, comprising administering to a patient in need thereof an effective amount of an agent which will antagonize the actions of endothelin (antisense to ET-mRNA, or ET antagonists, ECE antagonists).

By another aspect of this invention, there is provided a composition for use in the treatment of physiological conditions in which NO production is at least partially inhibited, comprising an effective amount of an endothelin antagonist or pharmaceutically acceptable salt thereof in admixture with a pharmaceutically acceptable carrier therefor.

In a preferred aspect, said physiological condition is erectile disfunction.

It will be appreciated that, in the experiments described below, an $ET_A/ET_B$ receptor antagonist was used in order to control for any transient vasodilation which might occur via an $ET_B$ receptor, and which would skew the estimation of involvement in hypertension following NO synthase blockade. It is believed, however, that $ET_A$ or $ET_B$ receptor antagonists alone would also, at least in part, suppress the endothelin induced vasoconstriction.

$ET_A$ and $ET_B$ antagonists are available commercially from various sources such as American Peptide Company Inc. and include:

| NAME | FORMULA | CAT NO. |
|---|---|---|
| | $ET_A$ | |
| Endothelin Antagonist | c(DTrp-DAsp-Pro-DVal-Leu) (SEQ ID NO: 1) | 88-2-10 |
| Endothelin Receptor Antagonist (BE18257B) | c(DGlu-Ala-AIlo-DIle-Leu-DTrp) (SEQ ID NO: 2) | 88-2-20 |
| Endothelin Antagonist (JKC-301) | c(DIle-Leu-DTrp-DAsp-Pro) (SEQ ID NO: 3) | 88-2-30 |
| Endothelin Antagonist (JKC-302) | c(DVal-Leu-DTrp-DSer-Pro) (SEQ ID NO: 4) | 88-2-31 |
| Endothelin Antagonist (BQ-610) | (N,N-hexamethylene)carbamoyl-Leu-DTrp(CHO)-DTrp (SEQ ID NO: 5) | 88-2-32 |
| Endothelin Receptor Antagonist (W-7338A) | c(DGlu-Ala-DVal-Leu-DTrp) (SEQ ID NO: 6) | 88-2-40 |
| | $ET_B$ | |
| [Cys11,Cys 15] Endothelin-1 (8–21), (1RL-1038) | c(DGlu-Ala-DVal-Leu-DTrp) (SEQ ID NO: 7) | 88-2-41 |
| [Ala11,15] Endothelin-1 (6–21), N-Acetyl | Ac-Leu-Met-Asp-Lys-Glu-Ala-Tyr-Phe-Ala-His-Leu-Asp-Ile-Ile-Trp (SEQ ID NO: 8) | 88-2-42 |
| N-Suc-[Glu9,Ala11,15] Endothelin-1, (8–21), (LRL-1620) | Suc-Asp-Glu-Glu-Ala-Val-Tyr-Phe-Ala-His-Leu-Asp-Ile-Ile-Trp (SEQ ID NO: 9) | 88-2-50 |

Figure 4:
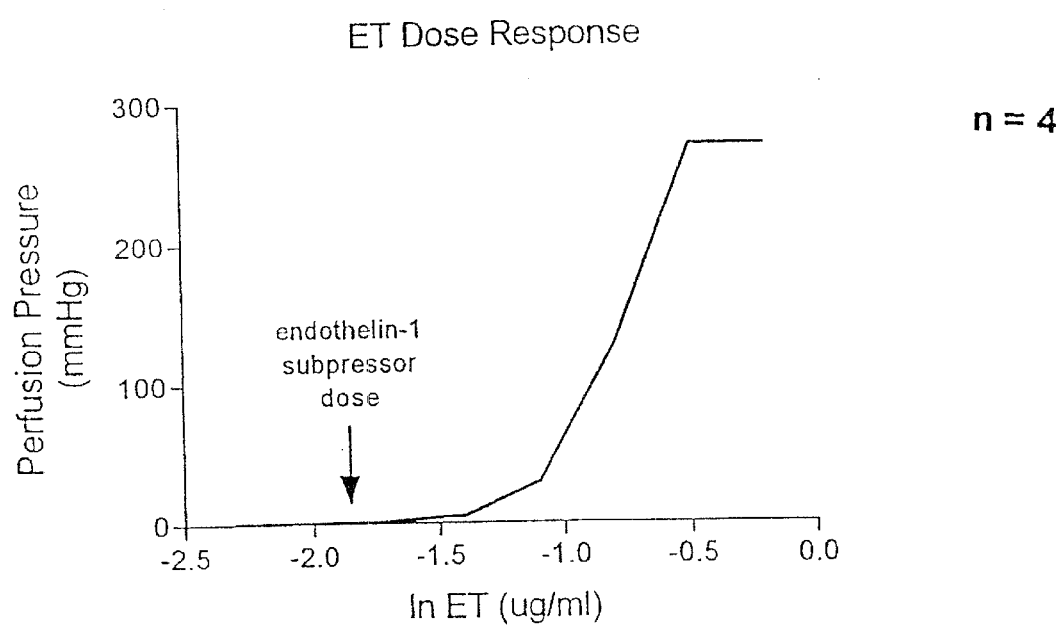

FIG. 4 is a graph illustrating the cumulative dose response to endothelin, n=4.

DETAILED DESCRIPTION OF PREFERRED EMBODIMENTS

It is known that, in vivo, several systems contribute to vascular tone and mean arterial pressure (MAP). These systems include the sympathetic nervous system (SNS), renin-angiotension system and the vasopressin system. As described in more detail hereinafter, the contribution of each of these different systems to an experimentally induced pressure increase of 30–40% in rats as a result of NO synthase (NOS) inhibition with $N^\omega$-nitro-L-arginine-methyl ester (L-NAME, Sigma Chemicals) has been assessed. If NO production is inhibited, a significant increase in MAP must be the result of endothelin release, since this MAP increase is eliminated when an endothelin antagonist is Methods Animals Male Sprague-Dawley rats (325–400 g) obtained from Charles River Laboratories (Montreal, Quebec, Canada) were housed individually under conditions of a 12 h light/12 h dark cycle, with room temperature at 22–24° C., and were provided with Purina Rodent Chow and tap water ad libitum for at least 2 days before any experiments were started.

Measurement of MAP and Short Acting Drug Administration

The surgical method was based on the technique of Thompson et al. (*Hypertension* 20: 809–815 (1992)). In brief, rats were anesthetized with ketamine/xylazine (70/5 mg/kg i.p.), and the descending aorta distal to the kidneys was catheterized with small bore TEFLON® tubing (0.012-in. i.d., o.d. 30 gauge, Cole-Parmer, Laval, Quebec, Canada) inserted into vinyl tubing (0.02-in. i.d., 0.060-in. o.d., 23 gauge). The inferior vena cava was also catheterized distal to the kidneys with small bore TEFLON® tubing (0.012-in. i.d., o.d. 30 gauge, Cole Parmer). The catheters were filled with heparinized saline (10 IU/mL) and held in place by a small amount of cyanoacrylate tissue glue at the puncture site. The catheters were tunneled subcutaneously and exteriorized at the back of the neck and sutured in place. Two days after surgery, MAP could be recorded (Narco Physiograph, E&I Instruments, Houston, Tex. or MacLab Data Acquisition System, ADInstruments, Milford, Mass., U.S.A.). After connection, an equilibration period of approximately 30 min was allowed for the determination of the steady state level of MAP before any recording began. Baseline MAP was determined from mean readings over 5 min, taken from each rat at 15 min intervals for at least 1 h prior to the start of any experiment. After obtaining a baseline MAP, the cumulative/sequential vasoconstrictor blockade was started, MAP values are expressed as an average MAP over 2–3 min following the establishment of a new steady state (i.e., MAP is no longer changing).
Experiment 1: Cumulative Vasoconstrictor Blockade Following Acute NO Inhibition NOS was inhibited by a single i.p. injection of $N^{\omega}$-nitro-L-arginine-methyl ester (L-NAME, Sigma, 100 mg/kg; 100 mg/mL 0.9% sterile saline solution, Baxter Corp., Toronto, Ontario, Canada). The $\alpha_1$-adrenoceptor antagonist prazosin® (Sigma Chemical Company, St. Louis, Mo., U.S.A.) at a dose of 1 mg/kg (in 0.9% saline and 5% ethanol [vol/vol], total volume 1 mL/kg) was used to block the majority of the SNS induced peripheral vasoconstriction. The non-peptide $AT_1$ receptor antagonist losartan® (Dupont-Merck, 30 mg/kg i.p.) was used to block the effects of Ang II. The $V_1/V_2$ receptor antagonist [β-mercapto-β, β-cyclopenta-methylenepropionyl, O-Et-Tyr$_2$-Val$_4$-Arg$_8$]-vasopressin (AVP) 20 µg/kg/min i.v., Sigma) was utilized to block the effects of vasopressin. The effects of the endothelin vasoconstrictor system, via $ET_A$ and $ET_B$ receptors, were blocked with a commercially available endothelin antagonist PD 145065 (100 mg/kg/min i.v., bolus, donated by Parke-Davis Pharmaceuticals). Each rat in the study received all of the aforementioned vasoconstrictor antagonists (i.e., a cumulative/sequential blockade). The addition of sodium nitroprusside (SNP) (200 µg/kg i.v. 0.3 c.c. bolus, Sigma) was used to transiently lower MAP to the level of minimum vascular resistance across all treatment groups (i.e., where the level of MAP becomes predominantly dependent on cardiac output at minimum vascular resistance; $MAP_{min}$= CO×$TPR_{min}$). Not surprisingly, this value was found to be similar across all treatment groups and enabled the calculation of the total range of MAP pressure lowering ($MAP_{range}$=MAP-$MAP_{min}$). As well, the addition of SNP reveals the activity of 'other' vasoconstrictor systems that might not have been accounted for but may be important in contributing to the level of MAP in control rats or after acute L-NAME treatment.

The selective blockers of the various vasoconstrictor systems were added in a cumulative and sequential manner in the following order: prazosin, losartan, AVP antagonist, PD 145065 and SNP. The interval between administration was up to 15 min, where a new steady state MAP had been established before the blockade of the next vasoconstrictor system.
Experiment 2: Effects of PD 145065 Before or After NOS Blockade After obtaining appropriate baseline steady-state levels of MAP, the effects of administration of losartan (30 mg/kg i.p., n=3, under 30 mg/kg i.p. pentabarbital anesthetic) or PD 145065 (10 mg/kg/min, i.v., n=6, conscious rats previously catheterized) on resting MAP and then on the L-NAME (100 mg/kg, i.p.)-induced pressor response were assessed in two ways. Administration of PD145065 was done prior to giving L-NAME to assess the effect on the normal circulation as well as on the development of the hypertension, whereas the administration after L-NAME-hypertension was already present was used to assess reversibility of the pressor response.

Data Analysis

All data are expressed as a peak MAP lowering as a mean ±S.D. Comparison of means between groups at each treatment level was done using a Student's T-test with the Bonferroni correction method, where appropriate.

Results

Figure 1:
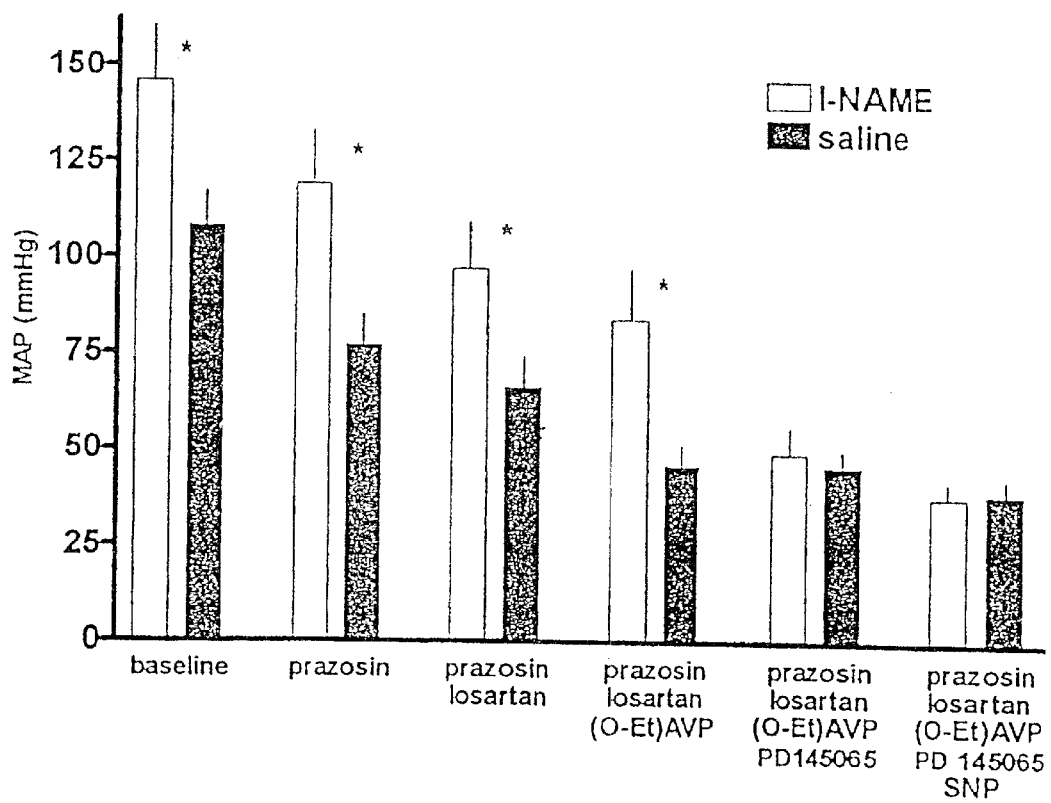
FIG. 1 is a block diagram illustrating MAP response with vasoconstrictor blockade (n=8, 8)

FIG. 1 illustrates the changes in steady state MAP responses following the sequential blockade of the vasoconstrictor systems in both the L-NAME (n=6) and saline control (n=6) groups. The steady state levels of MAP for saline and L-NAME-treated animals were 146±14 and 108±9 mmHg, respectively. The administration of large doses of prazosin®, losartan® and (O-ET) VAVP to antagonize the effects of 3 of the major vasoconstrictor systems lowered MAP by a similar extent in both the L-NAME (84±13 mmHg)- and saline (46±5 mmHg)-treated groups both on an absolute (delta MAP) and proportional (% of range) basis (Table 1 below) and yet there remained the same pressor response in the L-NAME group compared to control.

TABLE 1

| Blocking agent | Saline | | L-NAME | |
|---|---|---|---|---|
| | delta MAP | % of range | delta MAP | % of range |
| prazosin | 36 ± 6 | 48 ± 8 | 27 ± 14* | 25 ± 10* |
| losartan | 20 ± 6 | 27 ± 8 | 25 ± 13 | 24 ± 12 |
| (O-ET)VAVP | 21 ± 11 | 37 ± 15 | 19 ± 13 | 15 ± 9* |
| PD 145065 | 1 ± 2 | 1 ± 3 | 35 ± 13* | 39 ± 24* |
| SNP | 7 ± 3 | 12 ± 4 | 12 ± 9 | 4 ± 2 |

*denotes significant difference (p < 0.05) compared to saline control

The addition of PD 145065 to the saline-treated group following prazosin, losartan and (O-ET) VAVP administration did not significantly lower further the level of MAP (46±4 mmHg). In contrast, the addition of PD 145065 to the L-NAME-treated group under similar conditions dramatically lowered MAP from 84±13 mmHg to 46±7 mmHg. The administration of SNP further lowered MAP to 39±3 mmHg across all treatment groups, revealing a small component of other systems in both treatment groups.

Figure 2A:
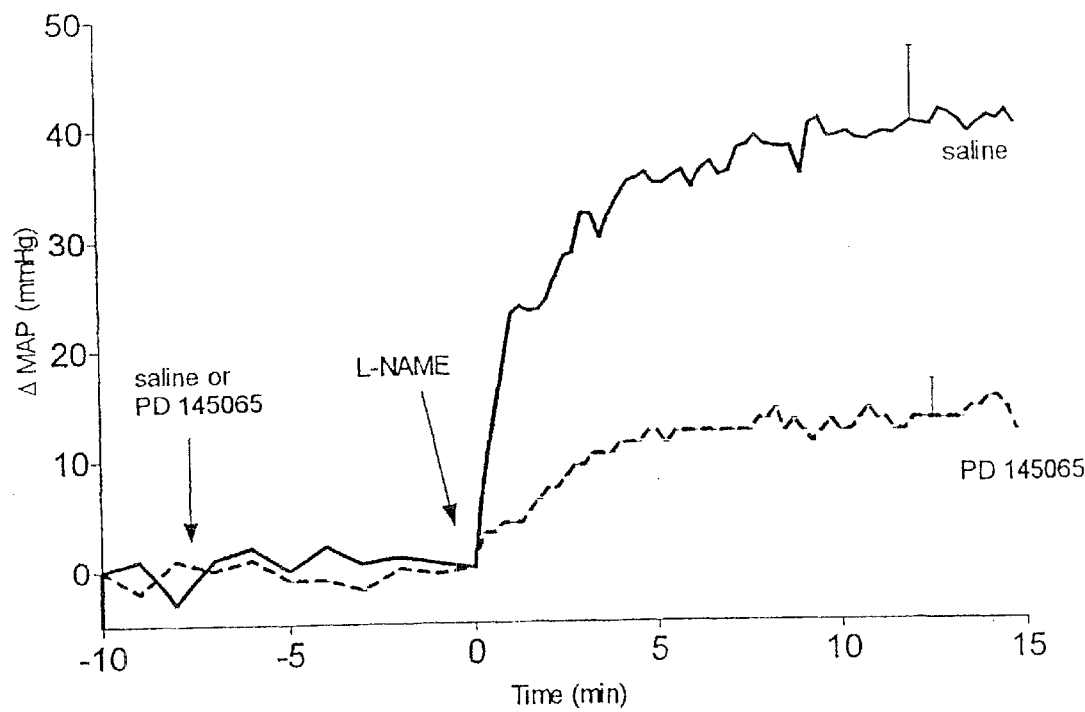
FIG. 2a is a graph illustrating MAP response with L-NAME pretreated with losartan or PD 145065, (n=6, 6)
Figure 2B:
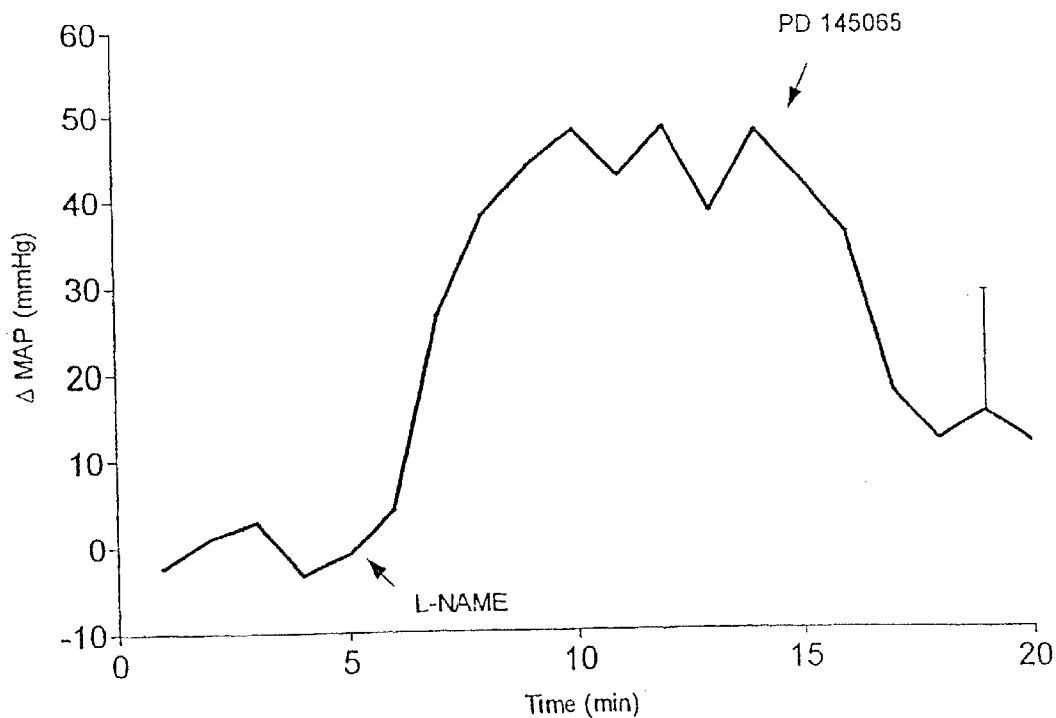
FIG. 2b is a graph illustrating MAP response after treatment with L-NAME followed by PD145065.

In Experiment 2, after obtaining appropriate baseline levels of MAP (100±15 mmHg), losartan treatment resulted in a lowering of MAP to 78±21 mmHg. In contrast, the administration of PD 145065 had no effect on the level of MAP (106±16 mmHg). There was a marked difference in the L-NAME pressure profile between the saline- and PD 145065-treated group (FIG. 2). The delta MAP responses 20 min after L-NAME treatment in the saline and PD 145065 pre-treatment groups were 40±8 and 11±7 mmHg, respectively (p<0.05).

The above experiments demonstrate that the contribution of the sympathetic nervous system, renin-angiotensin system and vasopressin system are not enhanced in the acute L-NAME induced hypertensive state, yet there remains a markedly enhanced vasoconstrictor tone (≈140%) compared to control. These studies also demonstrate that the pre-eminent mechanism of hypertension following acute NO synthase blockade is via endothelin-mediated vasoconstriction. This endothelin mechanism suggests that the prominent role of NO is to inhibit endothelin activity, likely by inhibiting its expression and release and not as a chronic direct acting vasodilator. Experiment 2 shows that pharmacological antagonism of the endothelin receptors does not change resting MAP, confirming previous studies that endothelin does not function as a prominent vasoconstrictor in normal circulating states.

There are, however, certain conditions which may be considered physiologically 'normal' but in which local levels of endothelin cause vasoconstriction, such as erectile responses in males. Administration of an A/B endothelin receptor antagonist in such circumstances will cause a desired local vasodilation and thus permit penile erection in an otherwise impotent male, and will decrease the potential for long term changes in vascular function and structure.

In situ Experimental Evidence for Endothelin as a 'Primer'

Three points regarding the mechanisms of endothelin involvement in erectile dysfunction have been described hereinabove. There is now presented in situ evidence to demonstrate that enhanced levels of endothelin markedly 'sensitize' the pudendal vascular bed to other vasoconstrictor systems. Stated another way, a slight enhancement of endothelin will synergistically enhance the impact of the sympathetic nervous system, i.e., a marked increase in vasoconstriction will result from even normal levels of sympathetic activation.

Figure 3:
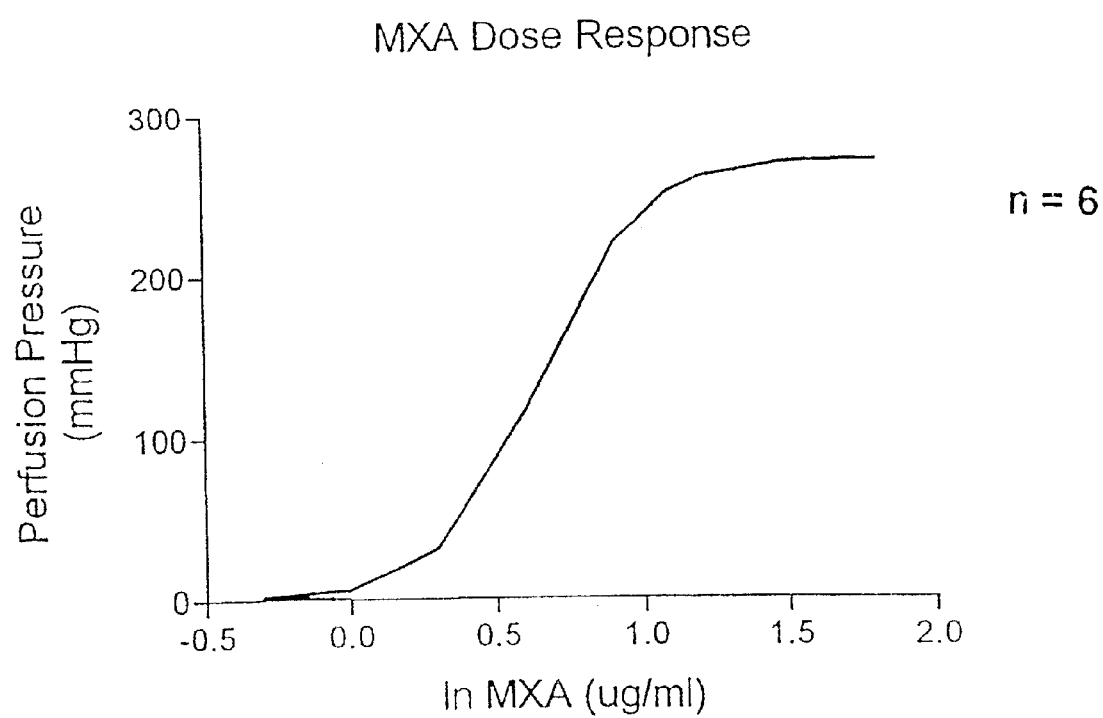
FIG. 3 is a graph illustrating the cumulative dose response to methoxamine, n=6; and added. Thus, it has been established that NO acts to chronically (locally) down-regulate the release of endothelin, not as a chronic direct acting vasodilator. The contribution of endothelin induced vasoconstriction to L-NAME hypertension was assessed by administering an $ET_A/ET_B$ receptor antagonist such as PD 145065 (Parke Davis Pharmaceuticals) in a pharmaceutically acceptable carrier therefor, both before and after NO synthase inhibitor "inhibition". Suitable carriers include water and isotonic dimethyl sulfoxide (DMSO). PD145065 is a peptide and hence not readily bioavailable by oral administration. Non-peptide receptor antagonists would be better choices for oral administration. PD145065 may be effectively administered by intravenous administration.

Vascular responses using the isolated perfusion of the pudendal vasculature preparation have been assessed. FIG. 3 illustrates the dose response curve to the α-adrenoceptor agonist methoxamine (MXA) alone. FIG. 4 illustrates the dose-response curve to endothelin alone. Table 2 represents the changes in perfusion pressure when low, sub-pressor doses of endothelin +MXA are given in comparision to MXA alone. These findings demonstrate that the MXA concentration-response (perfusion pressure) relationship was shifted to lower concentrations by more than 10-fold, i.e., when low doses of endothelin and MXA which alone are sub-pressor were combined, the effect was a pronounced increase in vascular resistance. These findings demonstrate that low level endothelin stimulation in the penile vasculature will result in synergism when α-adrenergic receptors are activated.

Methods

Animals

Male Wistar rats (400–500 g), obtained from Charles liver Laboratories (Montreal, Quebec, Canada), were housed individually under conditions of a 12 h light/12 h dark cycle (temperature of 22–24° C.), and were provided with Purina Rodent Chow and tap water ad libitum for at least two days before starting any experiment.

Pudendal Perfusion Preparation

The rats were anaesthetized with sodium pentabarbital (60 mg/kg i.p.) and the lower abdominal aorta was exposed through a mid-line incision. The isolation of the pudendal vasculature was developed by sequential ligation of all branches of the abdominal aorta not directly supplying the pudendal vasculature. The following arteries were dissected free and ligated: iliaca, femoralis, poplitea, glutea cranial, umbilicalis, epigastria caudal, pudenda external, glutea caudal, obturatoria, circumflexa femoris lateral, circumflexa femoris medial. After heparinization (1000 U/kg), the abdominal aorta was cannulated with a smooth, blunted 19-gauge needle. The arterial catheter was placed caudad into the aorta and the vena cava was cut and vented freely through the widely open abdominal cavity. The tip of the needle was advanced down the aorta to the iliac bifurcation and sutured in place. Flow of perfusate (0.5 mL/kg body weight/min) through the abdominal aorta was started immediately after transection, with sharp surgical scissors, of the abdominal aorta, inferior vena cava, spinal cord and all tissue 1 cm lateral to the spinal cord between $T_3$ and $T_7$ (FIG. 2). The perfusate was infused for 10 min, to flush the penile vasculature of blood, before starting any experiment.

The perfusate consisted of dextran (15%, average molecular weight, 71,400 Da, Sigma, St. Louis, Mo., U.S.A.) in Tyrode's solution (pH 7.4), which was aerated with 95% $O_2$ and 5% $CO_2$. The composition of the Tyrode's solution was KCl 20, $CaCl_2.2H_2O$ 32.3, $MgCl_2.6H_2O$ 5.1, $NaH_2PO_4.2H_2O$ 6.2, $NaHCO_3$ 100, and NaCl 800 mg per 100 mL fluid. The perfusate was held in a reservoir, and passed through a bubble trapping/mixing chamber and heating bath by an injection port located prior to the bubble trap for the introduction of pharmacological agents. An in-line peristaltic pump was used to establish flow at 0.5 mL/kg/min (Minipuls 2, Gilson Medical Elec., Inc., Middleton, Wis., U.S.A.). Added pharmacological agents, methoxamine (MXA) and sodium nitroprusside (SNP), were delivered by a syringe pump (Harvard Apparatus Infusion/Withdrawal Pump, Millis, Mass. U.S.A.). A servo-controlled heat chamber served to maintain rectal temperature at 36–38° C.

TABLE 2

A comparision of the perfusion pressure responses in control and endothelin subpressor treated rats to the $α_1$-adrenoceptor agonist methoxamine.

| [methoxamine μg/ml] | (Δ Perfusion Pressure (mmHg)) | |
|---|---|---|
| | Control | Endothelin sub-pressor |
| 0 | 0 | 0 |
| 0.1 | 0 | 0 |
| 0.25 | 0 | 34 ± 2 |
| 0.5 | 0 | 93 ± 30 |
| 1.0 | 4 ± 1 | 168 ± 16 |
| 2.0 | 11 ± 2 | — |
| 4.0 | 36 ± 11 | — |
| 8.0 | 67 ± 24 | — |

Values are expressed as group mean ±S.D., n=6 for control, n=4 for endothelin sub-pressor.

Experiment: Effects of Endothelin Antagonists on Blockade of Apomorphine-induced Erections It is well known that NOS blockers (e.g., L-NAME) inhibit erectile response acutely. According to our novel understanding of normal vascular biology as described herein, we proposed that the mechanism of L-NAME-induced erectile dysfunction, at least acutely, is dependent on the activation of endothelin (ET)-mediated vasoconstriction, and can thus be reversed with an ET antagonist. This was confirmed experimentally as described below.

Methods

Using the well-established apomorphine (APO)-induced erection model (apomorphine 80 μg/kg, administered subcutaneously), we counted the erections per 30 min interval in adult Wistar rats, per the protocol of Heaton, J. P. W., et al. (1991)(43). Rats were pretested with apomorphine alone to confirm and quantify normal erectile response (control Groups A and B). Rats were then treated with L-NAME (100 mg/kg, administered intraperitoneally) alone, acutely (at <1 h) and at 3 h; or the combination of $ET_{A/B}$ antagonist (PD 145065, 5 mg/kg/min, continuous intravenous infusion) +L-NAME.

Results

Data represent mean number of erections ±S.D. in the various different treatment groups. L-NAME alone blocked erection. Addition of the ET antagonist completely reversed acute L-NAME-induced decrease in erections, resulting in normal incidence of apomorphine-induced erections.

| Group-A (control) | Group-B (control) | L-NAME-acute | PD 145065 + L-NAME | L-NAME-3 h |
|---|---|---|---|---|
| 3.0 ± 1.31 | 2.5 ± 0.58 | 1.4 ± 0.74** | 2.5 ± 0.58 | 3.7 ± 1.38 |

**indicates significant difference from control ($p < 0.01$).

Conclusions

The mechanism of decreased erectile function following acute L-NAME involves increased endothelin-mediated vasoconstriction.

By this experiment in combination with the foregoing, the inventors provide proof of concept of their novel model of normal vascular biology and of the use of endothelin antagonists in down regulating local endothelin-mediated vasoconstrictor tone and vascular growth activity in a patient independently of any normal or abnormal systemic physiology.

All scientific publications cited herein are hereby incorporated by reference.

Although this invention is described in detail with reference to preferred embodiments thereof, these embodiments, like the experiments described herein, are offered to illustrate but not to limit the invention. It is possible to make other embodiments that employ the principles of the invention and that fall within its spirit and scope as defined by the claims appended hereto.

REFERENCES

1. Garg, U. C., and Hassid, A., *J. Biol. Chem.* 266: 9–12 (1991).
2. Garg, U. C., and Hassid, A., *J. Clin. Invest.* 83: 1774–1777 (1989).
3. Palmer, R. M. J., et al., *Nature* 327: 524–526 (1987).
4. Assender, J. W., et al., *J. Cardiovasc. Pharmacol.* 17(Suppl.3): S104–S107 (1991).
5. O'Conner, K. J., et al., *J. Cardiovasc. Pharmacol.* 17(Suppl.3): S100–S103 (1991).
6. Farhy, R. D., et al., *Circ. Res.* 72: 1202–1210 (1993).
7. Arnal, J. F., et al., *J. Clin. Invest.* 90: 647–652 (1992).
8. Manning, R. D., Jr., et al., *J. Hypertension* 21: 949–955 (1993).
9. Manning, R. D., Jr., et al., *J. Hypertension* 22: 40–48 (1993).
10. O'Conner, K. J., et al., *J. Cardiovasc. Pharmacol.* 17(Suppl.3): S100–S103 (1991).
11. Morton, J. J., et al., *J. Hypertension,* 11: 1083–1088 (1993).
12. Richard, V., et al., *Circ.* 91: 771–775 (1995).
13. Schiffrin, E. L., et al., *J. Hypertension* 25(2): 769–773 (1995).
14. Schiffrin, E. L., and Thibault, G., *Am. J. Hypertension* 4(1): 303–308 (1991).
15. Weber, H., et al., *Mol. Endo.* 8(2): 148–157 (1994).
16. Eddahibi, S., et al., *Am. J. Physiol.* 268(2): H828–835 (1995).
17. Kinsey, A. C., et al., "Sexual Behavior in the Human Male", W. B. Saunders: Philadelphia (1948).
18. Feldman, Henry A., et al., *J. Urol.* 151: 54–61 (1994).
19. Shabsigh, R., et al., *Urology* 32: 83–90 (1988).
20. Whitehead, E., *Geriatrics* 43(2): 114 (1988).
21. Furlow, W. L., et al., *Med. Aspects Human Sexuality* 19: 13–16 (1985).
22. Rajfer, J., et al., *New Engl. J. Med.* 326(2): 90–94 (1992).
23. Saenz de Tejada, I., et al., *Am. J. Physiol* 254: H459 (1988).
24. de Groat, W. C., and Steers, W. D., "Neuroanatomy and neurophysiology of penile erection" In: *Contemporary Management of Impotence and Infertility* (Tanagho, E. A., Lue, T. F., McClure, r. D., Eds.), Williams and Wilkins (1988).
25. Lue, T. F.,et al., *J. Urol.* 137(5): 829 (1987).
26. Juenemann, K. P., et al., *J. Urol.* 136(1):158 (1986).
27. Lue, T. F., et al., *J. Urol.* 130: 1237 (1983).
28. Weiss, H., et al., *Ann. Intern. Med.* 76: 793–799 (1980).
29. Jueneman, K. P., et al., *Br. J. Urol.* 64–84 (1989).
30. Melman, A., and Henry, D., *J. Urol.* 121: 419 (1979).
31. Benson, G. S., et al., *J. Clin. Invest.* 65: 506–513 (1980).
32. Hedlund, H., and Andersson, K. E., *J. Urol.,* 134: 1245 (1985).
33. Christ, G. J., et al., *J. Pharmacol.* 101: 375 (1990).
34. Wagner, G., and Brindley, G. S., "The effect of atrophine and c-blockers on human penile erection." In: *Vasculogenic Impotence* (Zorgniotti, A. W., Rossi, G., Eds.) Charles C. Thomas: Springfield, Ill., 77–81 (1980).
35. Adaikan, P. G., et al., *J. Auton. Pharm.* 3: 107 (1983).
36. Ignaro, L. J., et al., *Biochem. Biophys. Res. Commun.* 170: 843 (1990).
37. Gu, J., et al., *J. Urol.* 130: 386 (1983).
38. Gu, J., et al., *Lancet* 2: 315 (1984).
39. Willis, E., et al., *Life. Sci.* 33: 383 (1983).
40. Steif, C. G., et al., *J. Urol.* 143(2): 392–397 (1990).
41. Hedlund, H., and Andersson, K. E., *J. Urol.* 134: 1245 (1985).
42. Li, J.-S., and Schiffrin, E. L., *J. Hypertension* 13(6): 647–652 (1995).
43. Heaton, J. P. W., et al., *J. Urol.* 145: 1099–1102 (1991).

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Protein
        (B) LOCATION:1
        (D) OTHER INFORMATION:/pr oduct= "OTHER"
            /note= "D-Isomer of Tryptophan (DTrp)"

(ix) FEATURE:
        (A) NAME/KEY: Protein
        (B) LOCATION:2
        (D) OTHER INFORMATION:/pr oduct= "OTHER"
            /note= "D-Isomer of Aspartic Acid (DAsp)"

(ix) FEATURE:
        (A) NAME/KEY: Protein
        (B) LOCATION:4
        (D) OTHER INFORMATION:/pr oduct= "OTHER"
            /note= "D-Isomer of Valine (DVal)"

(xi) SEQUENCE DESCRIPTION: SEQ ID NO: 1:

Xaa Xaa Pro Xaa Leu
1               5

(2) INFORMATION FOR SEQ ID NO: 2:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Protein
        (B) LOCATION:1
        (D) OTHER INFORMATION:/pr oduct= "OTHER"
            /note= "D-Isomer of Glutamic Acid (DGlu)"

(ix) FEATURE:
        (A) NAME/KEY: Protein
        (B) LOCATION:3
        (D) OTHER INFORMATION:/pr oduct= "OTHER"
            /note= "Allo-D Isoleucine: alpha-carbon is D; beta-carbon
                is L"

(ix) FEATURE:
        (A) NAME/KEY: Protein
        (B) LOCATION:5
        (D) OTHER INFORMATION:/pr oduct= "OTHER"
            /note= "D-Isomer of Tryptophan (DTrp)"

(xi) SEQUENCE DESCRIPTION: SEQ ID NO: 2:

Xaa Ala Xaa Leu Xaa
1               5

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide

```
    (ix) FEATURE:
        (A) NAME/KEY: Protein
        (B) LOCATION:1
        (D) OTHER INFORMATION:/pr oduct= "OTHER"
            /note= "D-Isomer of Isoleucine (DIle)"

(ix) FEATURE:
        (A) NAME/KEY: Protein
        (B) LOCATION:3
        (D) OTHER INFORMATION:/pr oduct= "OTHER"
            /note= "D-Isomer of Tryptophan (DTrp)"

(ix) FEATURE:
        (A) NAME/KEY: Protein
        (B) LOCATION:4
        (D) OTHER INFORMATION:/pr oduct= "OTHER"
            /note= "D-Isomer of Aspartic Acid (DAsp)"

(xi) SEQUENCE DESCRIPTION: SEQ ID NO: 3:

Xaa Leu Xaa Xaa Pro
1               5

(2) INFORMATION FOR SEQ ID NO: 4:

(i) SEQUENCE CHARACTERISTICS:
        (A) LENGTH: 5 amino acids
        (B) TYPE: amino acid
        (C) STRANDEDNESS: single
        (D) TOPOLOGY: circular (ii) MOLECULE TYPE: peptide (ix) FEATURE:
        (A) NAME/KEY: Protein
        (B) LOCATION:1
        (D) OTHER INFORMATION:/pr oduct= "OTHER"
            /note= "D-Isomer of Valine (DVal)"

(ix) FEATURE:
        (A) NAME/KEY: Protein
        (B) LOCATION:3
        (D) OTHER INFORMATION:/pr oduct= "OTHER"
            /note= "D-Isomer of Tryptophan (DTrp)"

(ix) FEATURE:
        (A) NAME/KEY: Protein
        (B) LOCATION:4
        (D) OTHER INFORMATION:/pr oduct= "OTHER"
            /note= "D-Isomer of Serine (DSer)"

(xi) SEQUENCE DESCRIPTION: SEQ ID NO: 4:

Xaa Leu Xaa Xaa Pro
1               5

(2) INFORMATION FOR SEQ ID NO: 5:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION:1
        (D) OTHER INFORMATION:/pr oduct= "OTHER"
            /note= "Amino terminal-modified with (N,N-hexamethylene)
            carbamoyl"

(ix) FEATURE:
        (A) NAME/KEY: Protein
        (B) LOCATION:2
        (D) OTHER INFORMATION:/pr oduct= "OTHER"
```

/note= "D-Isomer of Tryptophan with formyl group on N of
              indole r ing (DTrp(CHO)"

(ix) FEATURE:
           (A) NAME/KEY: Protein
           (B) LOCATION:3
           (D) OTHER INFORMATION:/pr oduct= "OTHER"
              /note= "D-Isomer of Tryptophan (DTrp)"

(xi) SEQUENCE DESCRIPTION: SEQ ID NO: 5:

Leu Xaa Xaa
1

(2) INFORMATION FOR SEQ ID NO: 6:

(i) SEQUENCE CHARACTERISTICS:
           (A) LENGTH: 5 amino acids
           (B) TYPE: amino acid
           (C) STRANDEDNESS: single
           (D) TOPOLOGY: circular (ii) MOLECULE TYPE: peptide (ix) FEATURE:
           (A) NAME/KEY: Protein
           (B) LOCATION:1
           (D) OTHER INFORMATION:/pr oduct= "OTHER"
              /note= "D-Isomer of Glutamic Acid (DGlu)"

(ix) FEATURE:
           (A) NAME/KEY: Protein
           (B) LOCATION:3
           (D) OTHER INFORMATION:/pr oduct= "OTHER"
              /note= "D-Isomer of Valine (DVal)"

(ix) FEATURE:
           (A) NAME/KEY: Protein
           (B) LOCATION:5
           (D) OTHER INFORMATION:/pr oduct= "OTHER"
              /note= "D-Isomer of Tryptophan (DTrp)"

(xi) SEQUENCE DESCRIPTION: SEQ ID NO: 6:

Xaa Ala Xaa Leu Xaa
1               5

(2) INFORMATION FOR SEQ ID NO: 7:

(i) SEQUENCE CHARACTERISTICS:
           (A) LENGTH: 5 amino acids
           (B) TYPE: amino acid
           (C) STRANDEDNESS: single
           (D) TOPOLOGY: circular (ii) MOLECULE TYPE: peptide (ix) FEATURE:
           (A) NAME/KEY: Protein
           (B) LOCATION:1
           (D) OTHER INFORMATION:/pr oduct= "OTHER"
              /note= "D-Isomer of Glutamic Acid (DGlu)"

(ix) FEATURE:
           (A) NAME/KEY: Protein
           (B) LOCATION:3
           (D) OTHER INFORMATION:/pr oduct= "OTHER"
              /note= "D-Isomer of Valine (DVal)"

(ix) FEATURE:
           (A) NAME/KEY: Protein
           (B) LOCATION:5
           (D) OTHER INFORMATION:/pr oduct= "OTHER"
              /note= "D-Isomer of Trptophan (DTrp)"

(xi) SEQUENCE DESCRIPTION: SEQ ID NO: 7:

```
Xaa Ala Xaa Leu Xaa
1               5
```

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION:1
        (D) OTHER INFORMATION:/pr oduct= "OTHER"
            /note= "Amino group of Leucine is acetylated (Ac-Leu)"

(xi) SEQUENCE DESCRIPTION: SEQ ID NO: 8:

```
Leu Met Asp Lys Glu Ala Tyr Phe Ala His L eu Asp Ile Ile Trp
1               5                   10                  15
```

(2) INFORMATION FOR SEQ ID NO: 9:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION:1
        (D) OTHER INFORMATION:/pr oduct= "OTHER"
            /note= "Sucrose is attached to N-terminal of Aspartic
            Acid (Su c-Asp)"

(xi) SEQUENCE DESCRIPTION: SEQ ID NO: 9:

```
Asp Glu Glu Ala Val Tyr Phe Ala His Leu A sp Ile Ile Trp
1               5                   10
```

We claim:

1. A method for downregulating dothelin-mediated vascular growth activity of the pudendal vasculature in a patient independently of any normal or abnormal systemic physiology, comprising the step of administering to the patient an effective amount of an agent which antagonizes action of endothelin, in a pharmaceutically acceptable carrier therefor.

2. The method of claim 1 wherein said agent is selected from the group consisting of peptidal endothelin antagonists, non-peptidal endothelin antagonists, and inhibitors of endothelin converting enzyme.

3. The method of claim 1 wherein said agent is an $ET_A$ receptor antagonist.

4. The method of claim 1 wherein said agent is an $ET_B$ receptor antagonist.

5. The method of claim 1 wherein said agent is administered orally.

6. The method of claim 1 wherein said agent is administered intraperitoneally.

7. The method of claim 1 wherein said agent is an $ET_A/ET_B$ receptor antagonist.

8. The method of claim 7 wherein said $ET_A/ET_B$ receptor antagonist is PD145065.

9. The method of claim 8 wherein said PD145065 is administered intraperitoneally.

10. The method of claim 2 wherein said non-peptidal endothelin antagonist is bosentan.

11. The method of claim 2 wherein said inhibitor of endothelin converting enzyme is phosphoramidon.

* * * * *

UNITED STATES PATENT AND TRADEMARK OFFICE
CERTIFICATE OF CORRECTION

PATENT NO.     : 6,410,007 B1                                                          Page 1 of 1
DATED          : June 25, 2002
INVENTOR(S)    : James D. Banting, Jeremy P.W. Heaton and Michael A. Adams It is certified that error appears in the above-identified patent and that said Letters Patent is hereby corrected as shown below:

Column 21,
Line 45, please replace "dothelin" with -- endothelin --.

Signed and Sealed this

Ninth Day of December, 2003

JAMES E. ROGAN
*Director of the United States Patent and Trademark Office*